US009486421B2

(12) United States Patent
Lan-Hargest

(10) Patent No.: US 9,486,421 B2
(45) Date of Patent: *Nov. 8, 2016

(54) TREATMENT OF LUNG CELLS WITH HISTONE DEACETYLASE INHIBITORS

(75) Inventor: Hsuan-Yin Lan-Hargest, Fallston, MD (US)

(73) Assignee: ERRANT GENE THERAPEUTICS, LLC, Chicago, IL (US)

(*) Notice: Subject to any disclaimer, the term of this patent is extended or adjusted under 35 U.S.C. 154(b) by 21 days.

This patent is subject to a terminal disclaimer.

(21) Appl. No.: 12/003,511

(22) Filed: Dec. 26, 2007

(65) Prior Publication Data

US 2008/0312324 A1    Dec. 18, 2008

Related U.S. Application Data

(60) Continuation of application No. 10/715,377, filed on Nov. 19, 2003, now Pat. No. 7,314,953, which is a continuation-in-part of application No. 10/025,947, filed on Dec. 26, 2001, now Pat. No. 8,026,280, which is a continuation of application No. 09/812,940, filed on Mar. 27, 2001, now abandoned, said application No. 10/715,377 is a continuation-in-part of application No. 10/307,321, filed on Dec. 2, 2002, now abandoned, which is a division of application No. 09/812,944, filed on Mar. 27, 2001, now Pat. No. 6,495,719, said application No. 10/715,377 is a continuation-in-part of application No. 09/812,945, filed on Mar. 27, 2001, now Pat. No. 7,312,247.

(60) Provisional application No. 60/427,567, filed on Nov. 20, 2002.

(51) Int. Cl.
*C07C 57/60* (2006.01)
*C07C 259/06* (2006.01)
*C07D 307/54* (2006.01)
*A61K 31/16* (2006.01)
*A61K 31/19* (2006.01)
*C07C 57/42* (2006.01)

(52) U.S. Cl.
CPC .............. *A61K 31/16* (2013.01); *A61K 31/19* (2013.01); *C07C 57/42* (2013.01); *C07C 57/60* (2013.01); *C07C 259/06* (2013.01); *C07D 307/54* (2013.01)

(58) Field of Classification Search
CPC . A61K 31/165; C07D 307/54; C07C 259/06
See application file for complete search history.

(56) References Cited

U.S. PATENT DOCUMENTS

| 2,680,755 A | 6/1954 | Robeson et al. |
| 2,840,586 A | 6/1958 | Inhoffen |
| 3,479,396 A | 11/1969 | Buu-Hoi et al. |
| 3,551,574 A | 12/1970 | Frohberger et al. |
| 3,624,127 A | 11/1971 | Shaw et al. |
| 3,674,884 A | 7/1972 | Moritani et al. |
| 3,687,955 A | 8/1972 | Cerbati et al. |
| 3,755,604 A | 8/1973 | Gallo |
| 3,781,314 A | 12/1973 | Bollag et al. |
| 3,886,278 A | 5/1975 | Gallo |
| 3,909,353 A | 9/1975 | Tsuchida et al. |
| 3,978,100 A | 8/1976 | Fujita et al. |
| 3,984,440 A | 10/1976 | Bollag et al. |
| 4,011,339 A | 3/1977 | Galantay et al. |
| 4,024,182 A | 5/1977 | Kathawala |
| 4,044,149 A | 8/1977 | Fields et al. |
| 4,048,332 A | 9/1977 | Adams et al. |
| 4,061,656 A | 12/1977 | Klaus et al. |
| 4,081,476 A | 3/1978 | Anderson et al. |
| 4,113,858 A | 9/1978 | Hashim |
| 4,116,975 A | 9/1978 | Klaus et al. |
| 4,127,722 A | 11/1978 | Lafon |
| 4,127,723 A | 11/1978 | Yankee |
| 4,130,653 A | 12/1978 | Giroux et al. |
| 4,171,318 A | 10/1979 | Chan et al. |
| 4,188,338 A | 2/1980 | Bruins et al. |
| 4,193,931 A | 3/1980 | Loeliger |
| 4,211,783 A | 7/1980 | Shepherd |
| 4,258,057 A | 3/1981 | Bartmann et al. |
| 4,288,253 A | 9/1981 | Venable |
| 4,309,357 A | 1/1982 | Chiusoli et al. |
| 4,309,407 A | 1/1982 | Lautenschläger et al. |
| 4,335,054 A | 6/1982 | Blaser et al. |
| 4,355,168 A | 10/1982 | Chiusoli et al. |
| 4,371,614 A | 2/1983 | Anderson et al. |
| 4,388,459 A | 6/1983 | Shepherd |
| 4,439,443 A | 3/1984 | Giroux |
| 4,440,940 A | 4/1984 | Shepherd |

(Continued)

FOREIGN PATENT DOCUMENTS

| EP | 0 161 939 | 11/1985 |
| EP | 0 199 151 | 10/1986 |

(Continued)

OTHER PUBLICATIONS

Asmus et al, Journal of Allergy and Clinical Immunology, Pulmonary Function Response to EDTA, An Additive in Nebulized Bronchodilators, 2001, 107(1), pp. 68-72.*
Egan et al, American Journal of Respiratory Cell and Molecular Biology, Modulation of Ion Transport in Cultured Rabbit Tracheal Epithelium by Lipoxygenase, 1993, Metabolites, 795, pp. 500-506.*
Su et al, Molecular Cancer Therapeutics, Competitive or noncompetitive, that's the question: research toward histone deacetylase inhibitors, 2008, 7(5), pp. 1007-1112.*
Andrews et al., "Anti-malarial effect of histone deacetylation inhibitors and mammalian tumour cytodifferentiating agents," International Journal for Parasitology, 30, pp. 761-768, (2000).

(Continued)

*Primary Examiner* — Paul A Zucker
(74) *Attorney, Agent, or Firm* — Steptoe & Johnson LLP

(57) ABSTRACT

Lung disease, such as cystic fibrosis (CF), chronic obstructive pulmonary disease (COPD), asthma or acute and chronic bronchitis, can be treated with an oxyamide-containing compound.

4 Claims, No Drawings

(56) References Cited

U.S. PATENT DOCUMENTS

| | | | |
|---|---|---|---|
| 4,472,430 A | 9/1984 | Loev et al. |
| 4,504,494 A | 3/1985 | Grollier et al. |
| 4,505,930 A | 3/1985 | Loev et al. |
| 4,513,005 A | 4/1985 | Baker et al. |
| 4,534,979 A | 8/1985 | Loev et al. |
| 4,545,984 A | 10/1985 | Möller et al. |
| 4,564,476 A | 1/1986 | Ho |
| 4,604,407 A | 8/1986 | Haslanger et al. |
| 4,605,669 A | 8/1986 | Summers, Jr. |
| 4,607,053 A | 8/1986 | Karanewsky et al. |
| 4,608,390 A * | 8/1986 | Summers, Jr. ............... 514/575 |
| 4,619,945 A | 10/1986 | Loev et al. |
| 4,621,099 A | 11/1986 | Loev et al. |
| 4,623,661 A | 11/1986 | Summers, Jr. |
| 4,638,011 A | 1/1987 | Das |
| 4,663,336 A | 5/1987 | Nakane et al. |
| 4,699,920 A | 10/1987 | Skuballa et al. |
| 4,709,076 A | 11/1987 | Bombardelli et al. |
| 4,722,939 A | 2/1988 | Loev et al. |
| 4,731,382 A | 3/1988 | Zusi et al. |
| 4,753,934 A | 6/1988 | Nickl et al. |
| 4,791,133 A | 12/1988 | Djuric et al. |
| 4,820,828 A * | 4/1989 | Demers et al. ............... 549/362 |
| 4,833,257 A | 5/1989 | Pettit et al. |
| 4,950,467 A | 8/1990 | Phalangas et al. |
| 4,965,283 A | 10/1990 | Klessing et al. |
| 4,981,865 A | 1/1991 | Belliotti et al. |
| 4,985,436 A | 1/1991 | Pettit |
| 5,010,189 A | 4/1991 | Herold et al. |
| 5,028,629 A | 7/1991 | Hite et al. |
| 5,037,813 A | 8/1991 | Black et al. |
| 5,064,860 A | 11/1991 | Mueller et al. |
| 5,075,330 A | 12/1991 | Belliotti et al. |
| 5,084,214 A | 1/1992 | Kita et al. |
| 5,089,524 A | 2/1992 | Collins et al. |
| 5,091,569 A | 2/1992 | Matsumoto et al. |
| 5,112,846 A | 5/1992 | Belliotti et al. |
| 5,141,959 A | 8/1992 | Carroll et al. |
| 5,196,147 A | 3/1993 | Taketani et al. |
| 5,235,068 A | 8/1993 | Minai et al. |
| 5,244,922 A | 9/1993 | Burzynski |
| 5,246,955 A | 9/1993 | Skibo et al. |
| 5,264,424 A | 11/1993 | Della Valle et al. |
| 5,272,180 A | 12/1993 | Hashimoto et al. |
| 5,320,833 A | 6/1994 | Deckers et al. |
| 5,369,108 A | 11/1994 | Breslow et al. |
| 5,385,942 A | 1/1995 | Abe et al. |
| 5,420,160 A | 5/1995 | Gayer et al. |
| 5,466,718 A | 11/1995 | Nakatsu et al. |
| 5,475,022 A | 12/1995 | Chandraratna |
| 5,486,540 A | 1/1996 | Andrews |
| 5,525,629 A | 6/1996 | Criramin et al. |
| 5,534,654 A | 7/1996 | Ohtani et al. |
| 5,541,155 A | 7/1996 | Leone-Bay et al. |
| 5,547,988 A | 8/1996 | Yu et al. |
| 5,602,135 A | 2/1997 | Chandraratna |
| 5,607,978 A | 3/1997 | Woodward et al. |
| 5,643,949 A | 7/1997 | Van Scott et al. |
| 5,672,746 A | 9/1997 | Nau et al. |
| 5,677,320 A | 10/1997 | Chandraratna |
| 5,688,819 A | 11/1997 | Woodward et al. |
| 5,696,162 A | 12/1997 | Chandraratna |
| 5,705,167 A | 1/1998 | Bernardon et al. |
| 5,710,178 A | 1/1998 | Samid |
| 5,747,537 A | 5/1998 | Gordon et al. |
| 5,753,704 A | 5/1998 | Lindner et al. |
| 5,795,914 A | 8/1998 | Konno et al. |
| 5,804,601 A | 9/1998 | Kato et al. |
| 5,872,152 A | 2/1999 | Brown et al. |
| 5,883,124 A | 3/1999 | Samid |
| 5,891,737 A | 4/1999 | Baindur et al. |
| 5,908,868 A | 6/1999 | Buck et al. |
| 5,910,508 A | 6/1999 | Thoreau et al. |
| 5,910,606 A | 6/1999 | Foricher et al. |
| 5,932,606 A | 8/1999 | Isaacs et al. |
| 5,968,979 A | 10/1999 | Brusilow |
| 5,986,131 A | 11/1999 | Klaus et al. |
| 5,998,654 A | 12/1999 | Boehm et al. |
| 6,001,877 A | 12/1999 | Konno et al. |
| 6,004,988 A | 12/1999 | Amberg et al. |
| 6,030,993 A | 2/2000 | Jew et al. |
| 6,037,367 A | 3/2000 | Christensen, IV et al. |
| 6,043,389 A | 3/2000 | Nudelman et al. |
| 6,046,237 A | 4/2000 | Berge et al. |
| 6,057,369 A | 5/2000 | Groneberg et al. |
| 6,060,510 A | 5/2000 | Brusilow |
| 6,068,987 A | 5/2000 | Dulski et al. |
| 6,071,923 A | 6/2000 | Nudelman et al. |
| 6,083,984 A | 7/2000 | Brusilow |
| 6,110,697 A | 8/2000 | Dulski et al. |
| 6,110,955 A | 8/2000 | Nudelman et al. |
| 6,110,970 A | 8/2000 | Nudelman et al. |
| 6,124,495 A | 9/2000 | Neiss et al. |
| 6,147,224 A | 11/2000 | Vuligonda et al. |
| 6,376,508 B1 | 4/2002 | Li et al. |
| 6,451,334 B2 | 9/2002 | Perrine |
| RE37,947 E | 12/2002 | Bernardon et al. |
| 6,495,719 B2 * | 12/2002 | Lan-Hargest et al. ........ 562/621 |
| 6,511,990 B1 | 1/2003 | Breslow et al. |
| 7,312,247 B2 | 12/2007 | Lan-Hargest et al. |
| 7,314,953 B2 | 1/2008 | Wiech et al. |
| 2002/0143037 A1 | 10/2002 | Lan-Hargest et al. |
| 2003/0083521 A1 | 5/2003 | Lan-Hargest et al. |
| 2003/0195257 A1 | 10/2003 | Fanto et al. |
| 2004/0023944 A1 | 2/2004 | Lan-Hargest et al. |
| 2004/0029903 A1 | 2/2004 | Lan-Hargest et al. |

FOREIGN PATENT DOCUMENTS

| | | |
|---|---|---|
| GB | 2005271 | 4/1979 |
| JP | 53-101527 | 9/1978 |
| WO | WO98/55449 | 12/1998 |
| WO | WO99/29640 | 6/1999 |
| WO | WO 99/49860 A1 * | 10/1999 |
| WO | WO01/18171 | 3/2001 |
| WO | WO01/38322 | 5/2001 |
| WO | WO01/70675 | 9/2001 |
| WO | WO02/076941 | 10/2002 |
| WO | WO03/013493 | 2/2003 |
| WO | WO03/099272 | 12/2003 |

OTHER PUBLICATIONS

Collins et al., "Oral Sodium Phenylbutyrate Therapy in Homozygous β Thalassemia: A Clinical Trial," Blood, vol. 85, No. 1, pp. 43-49 (1995).

Finnin et al., "Structures of a histone deacetylase homologue bound to the TSA and SAHA inhibitors," Nature, vol. 401, pp. 188-193 (1999).

Fruehauf et al., "In Vitro Determination of Drug Response: A Discussion of Clinical Applications," Principles & Practice of Oncology, vol. 7 No. 12, pp. 1-16, (1993).

Gore et al., "Modifying histones to tame cancer: clinical development of sodium phenylbutyrate and other histone deacetylase inhibitors", Exp. Opin. Invest. Drugs, 9(12), pp. 2923-2934, (2000).

Hoffman et al., "A non-isotopic assay for histone deacetylase activity," Nucleic Acids Research, vol. 27, No. 9, pp. 2057-208 (1999).

Kemp et al., "Gene redundancy and pharmacological gene therapy: Implications for X-linked adrenoleukodystrophy," Nature Medicine, vol. 4, No. 11, pp. 1261-1268 (1998).

Kim et al., "Oxamflatin is a novel antitumor compound that inhibits mammalian histone deacetylase," Oncogene, vol. 18, pp. 2461-2470 (1999).

Marks et al., "Histone Deacetylase Inhibitors: Inducers of Differentiation or Apoptosis of Transformed Cell," Journal of the National Cancer Institute, vol. 92, No. 15, pp. 1210-1216 (2000).

Remiszewski et al., "Synthesis and in Vitro SAR of Straight Chain Hydroxamate Histone Deacetylase Inhibitors," Proceedings of the AACR, vol. 42, No. 4976 (Feb. 27, 2001).

(56) References Cited

OTHER PUBLICATIONS

Rubenstein et al., "In Vitro Pharmacologic Restoration of CFTR-mediated Chloride Transport with Sodium 4-Phenylbutyrate in Cystic Fibrosis Epithelial Cells Containing ΔF5O8-CFTR," J. Clin. Invest., vol. 100, No. 10, pp. 2457-2465 (1997).
Sandler et al., "Organic Functional Group Preparations," Academic Press, New York and London, vol. III, pp. 436-437 (1972).
Saunders et al., Histone deacetylase inhibitors: novel anticancer agents, Exp. Opin. Invest. Drugs, 8(10), pp. 1611-21 (1999).
Taunton et al., "A Mammalian Histone Deacetylase Related to the Yeast Transcriptional Regulator Rpd3p," Science, vol. 272, pp. 408-411 (1996).
Richon et al. "A class of hybrid polar inducers of transfomed cell differentiation inhibits histone deacetylase," Proc. Natl. Acad. Sci. Mar. 1998, vol. 95, No. 6, pp. 3003-3007, entire document.
Summers et al., "Hydroxamic Acid Inhibitors of 5-Lipoxygenase: Quantitative Structure-Activity Relationships," Journal of Medicinal Chemistry, 1990, vol. 33, pp. 992-998.
Egan et al., "Modulation of Ion Transport in Cultured Rabbit Tracheal Epithelium by Lipoxygenase," American Journal of Respiratory Cell and Molecular Biology, 1993, Metabolites, vol. 795, pp. 500-506.
Colwell et al., "5,5-Diarylpenta-2,4-dienoic Acid Amides as Potential Antimalarial Agents," Journal of Medicinal Chemistry, 1968, 11(4), pp. 749-752.
Fleming et al., "Decarboxylative Elimination of Enol Triflates as a General Synthesis of Acetylenes," Chemical Communications, 1999, pp. 1113-1114.
Linderman et al., "Enhanced Diastereoselectivity in the Asymmetric Ugi Reaction Using a New Convertible Isonitrile," Journal of Organic Chemistry, 1999, vol. 64, pp. 336-337.
Solomons, Organic Chemistry, 5$^{th}$ Edition, 1992, John Wiley & Sons, Inc., New York, pp. 796-798.
English translation of Hoorspool et al., "Preparation of Phenoxy Radicals," Monatshefte fuer Chemie, 1967, vol. 98(4), pp. 1256-1261.

Roedig et al., "Synthese and Thermische Umlagerung von cis-Pentachlopentadieonen zu Tetrachlorbutadiencarbonsaurechloriden," Annalen der Chemie, 1974, pp. 630-643 (with English abstract).
Kvita et al., Helvetica Chimica Acta, 1983, 66(8), pp. 2769-2777.
Jaeger et al., "Structure-activity Relationship Studies of Retinoid Cancer Inhibition," European Journal of Medicinal Chemistry, 1993, vol. 28, pp. 275-290.
Patel et al., "Palladium-cataylzed Arylation of Conjugated Dienes," Journal of Organic Chemistry, 1978, vol. 43(26), pp. 5018-5020.
Harding et al., "Synthesis of Some Polyfunctionalized Bicyclo[3.3.1]nonane-2,9-diones and Bicyclo[4.3.1]decane-2,10-diones," Journal of Organic Chemistry, 1981, vol. 46, pp. 940-948.
Horsham et al., "Metabolites of the Prototype Insecticide (2E,4E)-N-isobutyl-6-phenylhexa-2,4-dienamide. 1. Synthesis, Chromatography, Spectroscopy, and Biological Activity," J. Agric. Food Chem, 1989, vol. 37, pp. 777-781.
Posner et al. "Unsaturated compounds, VII. Addition of hydroxylamine to unsaturated acids with conjugated double linkages." Berichte der Deutschen Gesellschaft, 1911, vol. 43, p. 266-2676, CAPLUS Abstract, AN 1911:1749.
Howden et al., Journal of the American Chemical Society, Small Ring compounds. XLV, Influence of Vinyl and Phenyl Substituents on the Interconversion of Allylcarbinyl-Type Grignard Reagents, 88(8), p. 1732-1742 (1966).
Wittig et al., Berichte, 72B, p. 1387-1398 (1939), Abstract/Summary.
Hoorspool et al., Monatshefie fuer Chemie, Preparation of Phenoxy Radicals, 98(4), p. 1256-1261 (1967).
Meyer et al., "Omega-Substituted Alkyl Carboxylic Acids as Antidiabetic and Lipid-lowering agents," European Journal of Medicinal Chemistry, vol. 33, p. 775-787 (1998).
Scholz, "Beta-Keto Sulfones as Ethylene Carbanion Equivalents: The Synthesis of Unsaturated Carboxylic Acids," Liebigs Annalen der Chemie, vol. 2, p. 264-272 (1984).
Strunz et al., "Expedient Synthesis of Unsaturated Amide Alkaloids from Piper spp: Exploring the Scope of Recent Methodology," Canadian Journal of Chemistry, vol. 74, p. 419-432 (1996).

* cited by examiner

TREATMENT OF LUNG CELLS WITH HISTONE DEACETYLASE INHIBITORS

CROSS-REFERENCE TO RELATED APPLICATIONS

This application is a continuation of U.S. patent application Ser. No. 10/715,377, filed Nov. 19, 2003, issued as U.S. Pat. No. 7,314,953, which claims priority from U.S. provisional application Ser. No. 60/427,567, filed Nov. 20, 2002, and which is a continuation-in-part of U.S. patent application Ser. No. 10/025,947, filed Dec. 26, 2001, which is a continuation of U.S. patent application Ser. No. 09/812,940, filed Mar. 27, 2001, abandoned; U.S. patent application Ser. No. 10/307,321, filed Dec. 2, 2002, abandoned, which is a divisional of U.S. patent application Ser. No. 09/812,944, filed Mar. 27, 2001, issued as U.S. Pat. No. 6,495,719; and U.S. patent application Ser. No. 09/812,945, filed Mar. 27, 2001, issued as U.S. Pat. No. 7,312,247; all of which are incorporated herein by reference.

TECHNICAL FIELD

This invention relates to treatment of lung cells with histone deacetylase inhibitors.

BACKGROUND

Chronic obstructive pulmonary disease (COPD), or chronic obstructive lung disease, which includes chronic bronchitis and emphysema, can involve long-term (chronic) blockage or obstruction of the breathing tubes. The main physical change responsible for the problems encountered with the disease is the overproduction of mucous by the cells lining the larger breathing tubes (bronchi). This mucous can block the movement of air and contributes to the development of infections.

Cystic fibrosis (CF) is caused by a mutation in the gene that produces the protein that regulates movement of sodium ions and chloride ions through cell membranes. This protein is present in cells lining the passageways of the lungs, pancreas, colon, and genitourinary tract. When this protein is abnormal, the movement of chloride ions and water in the lung and other cells can become blocked, and there can be abnormal secretion of mucus.

Mucociliary clearance plays a critical role in the removal of inhaled debris and pathogens that enter the lung with each breath. Impaired mucociliary clearance and hypermucus secretion are two characteristics of a number of lung diseases including cystic fibrosis (CF), chronic obstructive pulmonary disease (COPD), asthma and acute and chronic bronchitis. Improving the clearance of mucus in patients suffering from or at risk of suffering from a lung disease can be of therapeutic benefit.

SUMMARY

Lung disease, such as cystic fibrosis (CF), chronic obstructive pulmonary disease (COPD), asthma or acute and chronic bronchitis, can be treated with a hydroxamic acid compound, or a pharmaceutical formulation including a hydroxamic acid compound. The treatment can include inhibiting a histone deacetylase in a cell. The inhibition of histone deacetylase in a cell is generally described, for example, in U.S. Pat. No. 6,495,719.

In one aspect, a method of inhibiting sodium ion transport in an airway epithelial cell includes contacting the cell with a compound including an oxyamide linkage in an amount effective to inhibit sodium ion transport. The compound can be of formula (I):

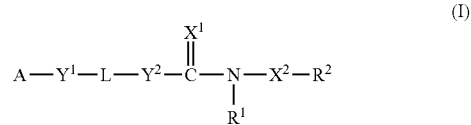

In certain circumstances, the cells can be contacted with a compound of formula (I) in vivo. In other circumstances, the cells are contacted with a compound of formula (I) in vitro.

In another aspect, a method of treating lung disease in a mammal includes administering to the mammal suffering from or at risk of suffering from the lung disease an effective amount of a compound including an oxyamide linkage, such as a compound of formula (I). The lung disease can be cystic fibrosis, chronic obstructive pulmonary disease, asthma, or acute and chronic bronchitis.

In another aspect, a method of treating cystic fibrosis in a mammal suffering from or at risk of suffering from cystic fibrosis includes administering to the mammal an effective amount of 5-phenyl-2,4-pentadienoylhydroxamic acid or 7-phenyl-2,4,6-heptatrienoylhydroxamic acid, or a pharmaceutically acceptable salt thereof.

In the compound of formula (I), A can be a cyclic moiety selected from the group consisting of $C_{3-14}$ cycloalkyl, 3-14 membered heterocycloalkyl, $C_{4-14}$ cycloalkenyl, 3-8 membered heterocycloalkenyl, aryl, or heteroaryl. The cyclic moiety can be optionally substituted with alkyl, alkenyl, alkynyl, alkoxy, hydroxyl, hydroxylalkyl, halo, haloalkyl, amino, alkylcarbonyloxy, alkyloxycarbonyl, alkylcarbonyl, alkylsulfonylamino, aminosulfonyl, or alkylsulfonyl. Alternatively, A can be a saturated branched $C_{3-12}$ hydrocarbon chain or an unsaturated branched $C_{3-12}$ hydrocarbon chain optionally interrupted by —O—, —S—, —N($R^a$)—, —C(O)—, —N($R^a$)—SO$_2$—, —SO$_2$—N($R^a$)—, —N($R^a$)—C(O)—O—, —O—C(O)—N($R^a$)—, —N($R^a$)—C(O)—N($R^b$)—, —O—C(O)—, —C(O)—O—, —O—SO$_2$—, —SO$_2$—O—, or —O—C(O)—O—, where each of $R^a$ and $R^b$, independently, is hydrogen, alkyl, alkenyl, alkynyl, alkoxy, hydroxylalkyl, hydroxyl, or haloalkyl. Each of the saturated and the unsaturated branched hydrocarbon chain can be optionally substituted with alkyl, alkenyl, alkynyl, alkoxy, hydroxyl, hydroxylalkyl, halo, haloalkyl, amino, alkylcarbonyloxy, alkyloxycarbonyl, alkylcarbonyl, alkylsulfonylamino, aminosulfonyl, or alkylsulfonyl.

In the compound of formula (I), each of $Y^1$ and $Y^2$, independently, is —CH$_2$—, —O—, —S—, —N($R^c$)—, —N($R^c$)—C(O)—O—, —O—C(O)—N($R^c$)—, —N($R^c$)—C(O)—N($R^d$)—, —O—C(O)—O—, or a bond. Each of $R^c$ and $R^d$, independently, can be hydrogen, alkyl, alkenyl, alkynyl, alkoxy, hydroxylalkyl, hydroxyl, or haloalkyl.

In the compound of formula (I), L is a straight $C_{2-12}$ hydrocarbon chain optionally containing at least one double bond, at least one triple bond, or at least one double bond and one triple bond. The hydrocarbon chain can be optionally substituted with $C_{1-4}$ alkyl, $C_{2-4}$ alkenyl, $C_{2-4}$ alkynyl, $C_{1-4}$ alkoxy, hydroxyl, halo, amino, nitro, cyano, $C_{3-5}$ cycloalkyl, 3-5 membered heterocycloalkyl, monocyclic aryl, 5-6 membered heteroaryl, $C_{1-4}$ alkylcarbonyloxy, $C_{1-4}$ alkyloxycarbonyl, $C_{1-4}$ alkylcarbonyl, or formyl. The hydrocarbon chain can be optionally interrupted by —O—, —N(R$^e$)—, —N(R$^e$)—C(O)—O—, —O—C(O)—N(R$^e$)—, —N(R$^e$)—C(O)—N(R$^f$)—, or —O—C(O)—O—. Each of R$^e$ and R$^f$, independently, can be hydrogen, alkyl, alkenyl, alkynyl, alkoxy, hydroxylalkyl, hydroxyl, or haloalkyl.

In the compound of formula (I), R$^1$ is hydrogen, alkyl, alkenyl, alkynyl, alkoxy, hydroxylalkyl, hydroxyl, haloalkyl, or an amino protecting group and R$^2$ is hydrogen, alkyl, hydroxylalkyl, haloalkyl, or a hydroxyl protecting group.

In certain circumstances, R$^1$ can be hydrogen, R$^2$ can be hydrogen, X$^1$ can be O, X$^2$ can be O, Y$^1$ can be —CH$_2$—, —O—, —N(R$^a$)—, or a bond, Y$^2$ can be —CH$_2$—, —O—, or —N(R$^c$)—, or A can be phenyl, furyl, thienyl, pyrrolyl, or pyridyl, for example, phenyl optionally substituted with alkyl, alkenyl, alkynyl, alkoxy, hydroxylalkyl, or amino.

In certain circumstances, L can be a saturated straight C$_{4-10}$ hydrocarbon chain substituted with C$_{1-4}$ alkyl, C$_{2-4}$ alkenyl, C$_{2-4}$ alkynyl, C$_{1-4}$ alkoxy, or amino, and further optionally interrupted by —O— or —N(R$^c$)—, L can be an unsaturated straight C$_{4-8}$ hydrocarbon chain containing 2-5 double bonds optionally substituted with C$_{1-4}$ alkyl, C$_{2-4}$ alkenyl, C$_{2-4}$ alkynyl, or C$_{1-4}$ alkoxy, and further being optionally interrupted by —O— or —N(R$^g$)—, or L can be —(CH═CH)$_m$— where m is 2 or 3, L being optionally substituted with C$_{1-4}$ alkyl, C$_{2-4}$ alkenyl, C$_{2-4}$ alkynyl, or C$_{1-4}$ alkoxy, and further being optionally interrupted by —O— or —N(R$^g$)—. R$^g$ can be hydrogen, alkyl, alkenyl, alkynyl, alkoxy, hydroxylalkyl, hydroxyl, or haloalkyl. For example, the compound can be 5-phenyl-2,4-pentadienoyl-hydroxamic acid or 7-phenyl-2,4,6-heptatrienoylhydroxamic acid.

As an alternative to a compound of formula (I), the compound can also be suberoylanilide hydroxamic acid (SAHA) or trichostatin.

The compound can be a pharmaceutically acceptable salt of the compound of formula (I). For example, a pharmaceutically acceptable salt can be formed when an amino-containing compound of this invention reacts with an inorganic or organic acid. Some examples of such an acid include hydrochloric acid, hydrobromic acid, hydroiodic acid, sulfuric acid, phosphoric acid, p-bromophenylsulfonic acid, carbonic acid, succinic acid, citric acid, benzoic acid, and acetic acid. Examples of pharmaceutically acceptable salts thus formed include sulfate, pyrosulfate bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, and maleate. A compound of this invention may also form a pharmaceutically acceptable salt when a compound of this invention having an acid moiety reacts with an inorganic or organic base. Such salts include those derived from inorganic or organic bases, e.g., alkali metal salts such as sodium, potassium, or lithium salts; alkaline earth metal salts such as calcium or magnesium salts; or ammonium salts or salts of organic bases such as morpholine, piperidine, pyridine, dimethylamine, or diethylamine salts.

It should be recognized that a compound of formula (I) can contain chiral carbon atoms. In other words, it may have optical isomers or diastereoisomers.

Alkyl is a straight or branched hydrocarbon chain containing 1 to 10 (preferably, 1 to 6; more preferably 1 to 4) carbon atoms. Examples of alkyl include, but are not limited to, methyl, ethyl, propyl, isopropyl, butyl, isobutyl, sec-butyl, tert-butyl, n-pentyl, 2-methylhexyl, and 3-ethyloctyl.

Alkenyl and alkynyl refer to a straight or branched hydrocarbon chain containing 2 to 10 carbon atoms and one or more (preferably, 1-4 or more preferably 1-2) double or triple bonds, respectively. Some examples of alkenyl and alkynyl include allyl, 2-butenyl, 2-pentenyl, 2-hexenyl, 2-butynyl, 2-pentynyl, and 2-hexynyl.

Cycloalkyl is a monocyclic, bicyclic or tricyclic alkyl group containing 3 to 14 carbon atoms. Some examples of cycloalkyl include cyclopropyl, cyclopentyl, cyclohexyl, cycloheptyl, adamantyl, and norbornyl. Heterocycloalkyl is a cycloalkyl group containing at least one heteroatom (e.g., 1-3) such as nitrogen, oxygen, or sulfur. The nitrogen or sulfur may optionally be oxidized and the nitrogen may optionally be quaternized. Examples of heterocycloalkyl include piperidinyl, piperazinyl, tetrahydropyranyl, tetrahydrofuryl, and morpholinyl. Cycloalkenyl is a cycloalkyl group containing at least one (e.g., 1-3) double bond. Examples of such a group include cyclopentenyl, 1,4-cyclohexa-di-enyl, cycloheptenyl, and cyclooctenyl groups. By the same token, heterocycloalkenyl is a cycloalkenyl group containing at least one heteroatom selected from the group of oxygen, nitrogen or sulfur.

Aryl is an aromatic group containing a 5-14 ring and can contain fused rings, which may be saturated, unsaturated, or aromatic. Examples of an aryl group include phenyl, naphthyl, biphenyl, phenanthryl, and anthracyl. If the aryl is specified as "monocyclic aryl," if refers to an aromatic group containing only a single ring, i.e., not a fused ring.

Heteroaryl is aryl containing at least one (e.g., 1-3) heteroatom such as nitrogen, oxygen, or sulfur and can contain fused rings. Some examples of heteroaryl include pyridyl, furanyl, pyrrolyl, thienyl, thiazolyl, oxazolyl, imidazolyl, indolyl, benzofuranyl, and benzthiazolyl.

The cyclic moiety can be a fused ring formed from two or more of the just-mentioned groups. Examples of a cyclic moiety having fused rings include fluorenyl, dihydro-dibenzoazepine, dibenzocycloheptenyl, 7H-pyrazino[2,3-c]carbazole, or 9,10-dihydro-9, 10-[2]buteno-anthracene.

Amino protecting groups and hydroxy protecting groups are well-known to those in the art. In general, the species of protecting group is not critical, provided that it is stable to the conditions of any subsequent reaction(s) on other positions of the compound and can be removed without adversely affecting the remainder of the molecule. In addition, a protecting group may be substituted for another after substantive synthetic transformations are complete. Examples of an amino protecting group include, but not limited to, carbamates such as 2,2,2-trichloroethylcarbamate or tertbutylcarbamate. Examples of a hydroxyl protecting group include, but not limited to, ethers such as methyl, t-butyl, benzyl, p-methoxybenzyl, p-nitrobenzyl, allyl, trityl, methoxymethyl, 2-methoxypropyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl, isobutyl, and n-pentyl; alkyl carbonates having from one to six carbon atoms and substituted with one or more halogen atoms such as 2,2,2-trichloroethoxymethyl and 2,2,2-trichloro-ethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other protecting groups and reaction conditions can be found in T. W. Greene, Protective Groups in Organic Synthesis, (3rd, 1999, John Wiley & Sons, New York, N.Y.).

Note that an amino group can be unsubstituted (i.e., —$NH_2$), mono-substituted (i.e., —NHR), or di-substituted (i.e., —$NR_2$). It can be substituted with groups (R) such as alkyl, cycloalkyl, heterocycloalkyl, aryl, heteroaryl, aralkyl, or heteroaralkyl. Halo refers to fluoro, chloro, bromo, or iodo.

Other features or advantages will be apparent from the following detailed description of several embodiments, and also from the appended claims.

DETAILED DESCRIPTION

A pharmaceutical composition including a compound of formula (I) can be used to treat disorders in lung cells, such as cystic fibrosis, COPD, asthma, and acute and chronic bronchitis. Cystic fibrosis can be characterized by hypersodium ion absorption and impaired chloride secretion. The altered ion migration can collapse volume of fluid in a layer over the epithelium, or the periciliary fluid, and cause a 2- to 4-fold decrease in mucociliary clearance. As a result, mucus and debris accumulate in the airways stimulating the further secretion of mucus. The further secretion of mucus can lead to the obstruction of airways. A lumenal membrane sodium channel called ENaC mediates sodium absorption in the airways. Chloride secretion is mediated by a lumenal membrane chloride channel called CFTR. Mutations in the gene coding for CFTR cause cystic fibrosis. COPD, asthma, and acute and chronic bronchitis are characterized by the hypersecretion of mucus that eventually leads to impaired mucociliary clearance.

Mucociliary clearance can be modulated pharmacologically. Pharmacological studies have shown that amiloride, a blocker of ENaC channels, and bikunin, an inhibitor of a protease that regulates ENaC, both cause the inhibition of sodium transport and increase mucociliary clearance.

Pharmacological agents that inhibit sodium transport in epithelial cells, and can be used in the treatment of lung disease including CF, COPD, asthma and acute and chronic bronchitis. For example, CF can be treated with pharmaceutical formulations that include compounds of formula (I). Since the initial defect in the majority of cases of CF is a reduced efficiency of mutant CF protein (CFTR) to exit the endoplasmic reticulum (ER), compounds of formula (I) are tested to evaluate their efficacy in increasing the trafficking of the CF protein out of the ER and its maturation through the Golgi. During its biosynthesis, CFTR is initially synthesized as a nascent polypeptide chain in the rough ER, with a molecular weight of around 120 kDa (Band A). It rapidly receives a core glycosylation in the ER, giving it a molecular weight of around 140 kDa (Band B). As CFTR exits the ER and matures through the Golgi stacks, its glycosylation is modified until it achieves a terminal mature glycosylation, affording it a molecular weight of around 170 kDa (Band C). Thus, the extent to which CFTR exits the ER and traverses the Golgi to reach the plasma membrane may be reflected in the ratio of Band B to Band C protein. CFTR is immunoprecipitated from control cells, and cells exposed to test compounds. Both wt CFTR and ΔF508 CFTR expressing cells are tested. Following lysis, CFTR are immunoprecipitated using various CFTR antibodies. Immunoprecipitates are then subjected to in vitro phosphorylation using radioactive ATP and exogenous protein kinase A. Samples are subsequently solubilized and resolved by SDS-PAGE. Gels are then dried and subject to autoradiography and phosphor image analysis for quantitation of Bands B and C as determined on a BioRad personal fix image station.

The compounds of formula (I) can be prepared as follows. A carboxylic acid-containing compound of the present invention can be prepared by any known methods in the art. For example, a compound of the invention having an unsaturated hydrocarbon chain between A and —C(=$X^1$)— can be prepared according to the following scheme:

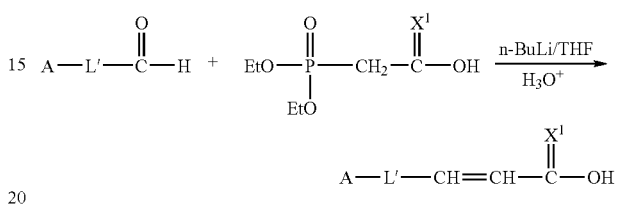

where L' is a saturated or unsaturated hydrocarbon linker between A and —CH=CH— in a compound of the invention, and A and $X^1$ has the same meaning as defined above. See Coutrot et al., Syn. Comm. 133-134 (1978). Briefly, butyllithium is added to an appropriate amount of anhydrous tetrahydrofuran (THF) at a very low temperature (e.g., −65° C.). A second solution having diethylphosphonoacetic acid in anhydrous THF is added dropwise to the stirred butyllithium solution at the same low temperature. The resulting solution is stirred at the same temperature for an additional 30-45 minutes which is followed by the addition of a solution containing an aromatic acrylaldehyde in anhydrous THF over 1-2 hours. The reaction mixture is then warmed to room temperature and stirred overnight. It is then acidified (e.g., with HCl) which allows the organic phase to be separated. The organic phase is then dried, concentrated, and purified (e.g., by recrystallization) to form an unsaturated carboxylic acid.

Alternatively, a carboxylic acid-containing compound can be prepared by reacting an acid ester of the formula A-L'—C(=O)—O— lower alkyl with a Grignard reagent (e.g., methyl magnesium iodide) and a phosphorus oxychloride to form a corresponding aldehyde, which can be further oxidized (e.g., by reacting with silver nitrate and aqueous NaOH) to form an unsaturated carboxylic acid.

Other types of carboxylic acid-containing compounds (e.g., those containing a linker with multiple double bonds or triple bonds) can be prepared according to published procedures such as those described, for example, in Parameswara et al., Synthesis, 815-818 (1980) and Denny et al., J Org. Chem., 27, 3404 (1962).

Carboxylic acid-containing compounds can then be converted to hydroxamic acid-containing compounds according to the following scheme:

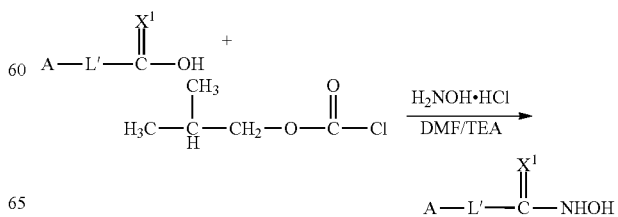

Triethylamine (TEA) is added to a cooled (e.g., 0-5° C.) anhydrous THF solution containing the carboxylic acid. Isobutyl chloroformate is then added to the solution having carboxylic acid, which is followed by the addition of hydroxylamine hydrochloride and TEA. After acidification, the solution is filtered to collect the desired hydroxamic acid.

An N-substituted hydroxamic acid can be prepared in a similar manner as described above. A corresponding carboxylic acid A-L'—C(=O)—OH can be converted to an acid chloride by reacting with oxalyl chloride (in appropriate solvents such as methylene chloride and dimethylformamide), which in turn, can be converted to a desired N-substituted hydroxamic acid by reacting the acid chloride with an N-substituted hydroxylamine hydrochloride (e.g., $CH_3NHOH \cdot HCl$) in an alkaline medium (e.g., 40% NaOH (aq)) at a low temperature (e.g., 0-5° C.). The desired N-substituted hydroxamic acid can be collected after acidifying the reaction mixture after the reaction has completed (e.g., in 2-3 hours).

As to compounds of the invention wherein $X^1$ is S, they can be prepared according to procedures described in Sandler, S. R. and Karo, W., *Organic Functional Group Preparations, Volume III* (Academic Press, 1972) at pages 436-437. For preparation of compounds of the invention wherein $X^2$ is —N(R$^c$)OH— and $X^1$ is S, see procedures described in U.S. Pat. Nos. 5,112,846, 5,075,330 and 4,981,865.

Compounds of the invention containing an α-keto acid moiety (e.g., when $X^1$ is oxygen and $X^2$ is —C(=O)OM or A-L'—C(=O)—C(=O)—OM, where A and L' have been defined above and M can be hydrogen, lower alkyl or a cation such as $K^+$) can be prepared by procedures based on that described in Schummer et al., *Tetrahedron*, 43, 9019 (1991). Briefly, the procedure starts with a corresponding aldehyde-containing compound (e.g., A-L'—C(=O)—H), which is allowed to react with a pyruvic acid in a basic condition (KOH/methanol) at a low temperature (e.g., 0-5° C.). Desired products (in the form of a potassium salt) are formed upon warming of the reaction mixture to room temperature.

The compounds described above, as well as their (thio) hydroxamic acid or α-keto acid counterparts, can possess histone deacetylase inhibitory properties.

Note that appropriate protecting groups may be needed to avoid forming side products during the preparation of a compound of the invention. For example, if the linker L' contains an amino substituent, it can be first protected by a suitable amino protecting group such as trifluoroacetyl or tert-butoxycarbonyl prior to being treated with reagents such as butyllithium. See, e.g., T. W. Greene, supra, for other suitable protecting groups.

A compound produced by the methods shown above can be purified by flash column chromatography, preparative high performance liquid chromatography, or crystallization.

An effective amount is defined as the amount which is required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.* 50, 219 (1966). Body surface area may be approximately determined from height and weight of the patient. See, e.g., *Scientific Tables*, Geigy Pharmaceuticals, Ardsley, N.Y., 1970, 537. An effective amount of a compound described herein can range from about 1 mg/kg to about 300 mg/kg. Effective doses will also vary, as recognized by those skilled in the art, dependant on route of administration, excipient usage.

The pharmaceutical composition may be administered by a parenteral route, for example, orally, topically, subcutaneously, intraperitoneally, intramuscularly, intravenously or by inhalation. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the therapeutic compounds. Because some of the compounds described herein can have limited water solubility, a solubilizing agent can be included in the composition to improve the solubility of the compound. For example, the compounds can be solubilized in polyethoxylated castor oil (Cremophor EL®) and may further contain other solvents, e.g., ethanol. Furthermore, compounds described herein can also be entrapped in liposomes.

A compound described herein can be formulated into dosage forms for other routes of administration utilizing conventional methods. For example, it can be formulated in a capsule, a gel seal, or a tablet for oral administration. Capsules may contain any standard pharmaceutically acceptable materials such as gelatin or cellulose. Tablets may be formulated in accordance with conventional procedures by compressing mixtures of a compound described herein with a solid carrier and a lubricant. Examples of solid carriers include starch and sugar bentonite. Compounds of this invention can also be administered in a form of a hard shell tablet or a capsule containing a binder, e.g., lactose or mannitol, a conventional filler, and a tableting agent. Alternatively, the compound can be administered in a nanoparticle, liposome or other formulation suitable for inhalation.

The toxicity of a compound described herein can be evaluated when a compound of formula (I) is administered by single intraperitoneal dose to test mice. After administration of a predetermined dose to three groups of test mice and untreated controls, mortality/morbidity checks are made daily. Body weight and gross necropsy findings are also monitored. For reference, see Gad, S. C. (ed.), *Safety Assessment for Pharmaceuticals* (Van Nostrand Reinhold, N.Y., 1995).

Without further elaboration, it is believed that one skilled in the art can, based on the description herein, utilize the present invention to its fullest extent. The following specific examples, which describe syntheses, screening, and biological testing of various compounds of this invention, are therefore, to be construed as merely illustrative, and not limitative of the remainder of the disclosure in any way whatsoever. All publications recited herein, including patents, are hereby incorporated by reference in their entirety.

Example 1

Synthesis of 7-phenyl-2,4,6-heptatrienoic acid

To a cooled (0-55° C.) 927 mL of 1 M solution of phenyl magnesium bromide in tetrahydrofuran was added dropwise a solution of crotonaldehyde (65.0 g) in 130 mL of anhydrous ether over a period of 2 hours and 45 minutes. The reaction was stirred for an additional 45 minutes and then warmed to room temperature. After four more hours of stirring, saturated ammonium chloride aqueous solution (750 mL) was added to the reaction. The mixture was extracted with 750 mL of ether twice. The combined extract was dried over anhydrous potassium carbonate and filtered. The solvent was evaporated to give 135.88 g (99.9%) of the desired 1-phenyl-2-buten-1-ol as an oil which was used in the next step without further purification.

1-Phenyl-2-buten-1-ol (135.88 g) was dissolved in 2300 mL of dioxane and treated with 2750 mL of dilute hydrochloric acid (2.3 mL of concentrated hydrochloric acid in 2750 mL of water) at room temperature. The mixture was stirred overnight and then poured into 4333 mL of ether and neutralized with 2265 mL of saturated aqueous sodium bicarbonate. The aqueous phase was extracted with 1970 mL of ether. The combined extract was dried over anhydrous potassium carbonate. Evaporation of the solvent followed by Kugelrohr distillation at 30° C. for 30 minutes afforded 131.73 g (96.8%) of the desired 4-phenyl-3-buten-2-ol as an oil which was used in the next step without further purification.

Dimethylformamide (DMF, anhydrous, 14 mL) was cooled to 0-5° C. and phosphorus oxychloride (8.2 mL) was added dropwise over a period of 40 minutes. The resulting solution was added dropwise to a cooled (0-5° C.) solution of 4-phenyl-3-buten-2-ol (10 g) in 32 mL of anhydrous DMF over a period of an hour. The reaction mixture was warmed to room temperature over a 35-minute period and then gradually heated up to 80° C. over a period of 45 minutes. The reaction was stirred at 80° C. for three hours and then cooled to 0-5° C. To the cooled reaction solution was added dropwise a solution of sodium acetate (40 g) in deionized water (100 mL) over a period of one hour. The mixture was then reheated to 80° C., stirred at 80° C. for an additional 10 minutes, cooled down to room temperature and extracted with ether (100 mL) twice. The combined extract was washed with brine (100 mL), dried over anhydrous sodium sulfate, filtered and concentrated under vacuum to yield 8.78 g of the desired 5-phenyl-2,4-pentadienal as a liquid which was used in the next step without further purification. $^1$H NMR (CDCl$_3$, 300 MHz), δ(ppm) 7.51 (m, 2H), 7.37 (m, 3H), 7.26 (m, 1H), 7.01 (m, 2H), 6.26 (m, 1H).

Butyllithium (12.8 mL of 2.5 N solution) was added to 65 mL of anhydrous tetrahydrofuran (THF) at −65° C. A solution of diethylphosphonoacetic acid (2.92 g) in 25 mL of anhydrous THF was added dropwise to the stirred solution at −65° C. The resulting solution was stirred at −65° C. for an additional 30 minutes and then a solution of 5-phenyl-2,4-pentadienal (2.4 g) in 15 mL of anhydrous THF was added to the reaction at −65° C. The reaction was stirred for one hour, allowed to warm to room temperature and then stirred overnight. To the reaction was added 30 mL of water, acidified with 5% hydrochloric acid (14 mL) to a pH of 4.7 and then added an additional 20 mL of water. The aqueous layer was extracted with 10 mL of ether twice and with 10 mL of ethyl acetate once. The combined organic extract was dried over anhydrous sodium sulfate, filtered and concentrated under vacuum. The crude material was dissolved in 50 mL of hot methanol and then refrigerated overnight. The crystals formed were filtered and dried under vacuum to afford 2.4 g of the desired 7-phenyl-2,4,6-heptatrienoic acid. $^1$H NMR (DMSO-d$_6$, 300 MHz), δ(ppm) 7.52 (m, 2H), 7.33 (m, 4H), 7.06 (m, 1H), 6.86 (m, 2H), 6.58 (m, 1H), 5.95 (d, 1H).

Example 2

Synthesis of 5-phenyl-2,4-pentadienoylhydroxamic acid

Triethylamine (TEA, 29 mL) was added to a cooled (0-5° C.) solution of 5-phenyl-2,4-pentadienoic acid (29.0 g) in 300 mL of anhydrous dimethylformamide. To this solution was added dropwise isobutyl chloroformate (27.0 mL). The reaction mixture was stirred for 15 minutes and hydroxylamine hydrochloride (28.92 g) was added followed by dropwise addition of 58 mL of TEA over a period of 60 minutes at 0-5° C. The reaction was allowed to warm to room temperature and stirred overnight. The reaction was then poured into 450 mL of a 1% (by weight) solution of citric acid and then extracted with 200 mL of methylene chloride twice and 500 mL of ether once. The solvents were removed under vacuum to give an oil. The crude oil was crystallized with 200 mL of hot acetonitrile to give a tan solid. The tan solid was recrystallized from 60 mL of hot acetonitrile to afford 12.5 g of the desired 5-phenyl-2,4-pentadienoylhydroxamic acid. $^1$H NMR (DMSO-d$_6$, 300 MHz), δ(ppm) 7.56 (d, 2H), 7.31 (m, 4H), 7.03 (m, 2H), 6.05 (s, 1H).

Example 3

Synthesis of 7-phenyl-2,4,6-heptatrienoylhydroxamic acid

Triethylamine (TEA, 24.1 mL) was added to a cooled (0-5° C.) solution of 7-phenyl-2,4,6-heptatrienoic acid (27.8 g) in 280 mL of anhydrous dimethylformamide. To this solution was added dropwise isobutyl chloroformate (22.5 mL) over a period of 75 minutes. The reaction mixture was stirred for 40 minutes and hydroxylamine hydrochloride (24.2 g) was added followed by dropwise addition of 48 mL of TEA over a period of 70 minutes at 0-5° C. The reaction was allowed to warm to room temperature and stirred overnight. To the stirred reaction mixture at room temperature was added 280 mL of a 1% (by weight) solution of citric acid followed by 1050 mL of water. The mixture was stirred for 30 minutes and then filtered. The filtered cake was washed with water (200 mL) and dried under vacuum to afford 20.5 g of the desired 7-phenyl-2,4,6-heptatrienoylhydroxamic acid. $^1$H NMR (DMSO-d$_6$, 300 MHz), δ(ppm) 7.48 (m, 2H), 7.32 (m, 2H), 7.19 (m, 2H), 7.01 (m, 1H), 6.75 (m, 2H), 6.51 (m, 1H), 5.93 (d, 1H).

Example 4

Cystic Fibrosis Screening Assay

As described above, during its biosynthesis, CFTR is initially synthesized as a nascent polypeptide chain in the rough ER, with a molecular weight of around 120 kDa (Band A). It rapidly receives a core glycosylation in the ER, giving it a molecular weight of around 140 kDa (Band B). As CFTR exits the ER and matures through the Golgi stacks, its glycosylation is modified until it achieves a terminal mature glycosylation, affording it a molecular weight of around 170 kDa (Band C). The extent to which CFTR exits the ER and traverses the Golgi to reach the plasma membrane may be reflected in the ratio of Band B to Band C protein. CFTR was immunoprecipitated from control cells and cells exposed to test compounds. Both wt CFTR and ΔF508 CFTR expressing cells were tested. Following lysis, CFTR was immunoprecipitated using various CFTR antibodies. Immunoprecipitates were then subjected to in vitro phosphorylation using radioactive ATP and exogenous protein kinase A. Samples were subsequently solubilized and resolved by SDS-PAGE. Gels were then dried and subject to autoradiography and phosphor image analysis for quantitation of Bands B and C as determined on a BioRad personal fix image station.

Cell Culture

Chinese hamster ovary (CHO) cells stably expressing both wt and ΔF508 CFTR were used in these assays. The cultures were grown on 100 mm plastic cell dishes in DMEM containing 10% foetal bovine serum (FBS) and kept at 5% $CO_2$/95% $O_2$ at 37° C. Cells were grown to confluence and used 3-5 days post-plating. Compounds of formula (I) were added to cells for 24 hours prior to analysis.

Immunoprecipitation

Cells were treated with test compounds and CFTR immunoprecipitated as described in Bradbury et al., *Am. J. Physiol.* 276, L659-668 (1999). Briefly, treated cells were lysed in buffer containing 1% TRITON X-100 and various protease inhibitors. Soluble material was immunoprecipitated using both R domain and C-terminal monoclonal antibodies. Immunoprecipitated CFTR was then subject to in vitro phosphorylation using camp-dependent PKA catalytic subunit and [γ-$^{32}$P]ATP, followed by resolution on SDS-PAGE gels. After fixation, the gels were dried and processed for autoradiography and phosphor image analysis. Quantitation of B and C bands was determined on a BioRad personal fix image analysis station.

It was found that compounds of the invention (at 100 μM) showed no significant changes in the levels of Bands B and C in treated cells relative to untreated cells. Based on the results obtained from using these test compounds, there was no gross effect of the test compounds on the expression levels of wild type CFTR. Analysis of band C of ΔF508 CFTR CHO cells showed that very little Band C was present in ΔF508 cells compared to wild-type cells. Exposure of these cells to test compounds at 100 μM for 24 hours at 37° C. did not affect the level of Band C CFTR in either wild-type or ΔF508 CFTR expressing cells. In contrast, analysis of Band B CFTR inu ΔF508 cells showed that test compounds at 100 μM resulted in a significant increase (about 6-7 fold) in the level of Band B compared to ΔF508 cells not exposed to the test compounds. Data are presented in Table 1.

TABLE 1

| Experimental Condition | % Band B relative to non-treated cells (mean + SEM) n = 4 | % Band C relative to non-treated cells (mean + SEM) n = 4 |
|---|---|---|
| Wild type CFTR (non-treated) | 274.97 ± 15.21 | 2812 ± 19.5 |
| ΔF508 (non-treated) | 100 ± 5.4 | 100 ± 6.25 |
| ΔF508 + 5-phenyl-2,4-pentadienoylhydroxamic acid | 635.2 ± 15.4 | 110.16 ± 5.20 |
| ΔF508 + 5-phenyl-2,4-pentadienoic acid | 93.2 ± 11.25 | 98.47 ± 10.25 |

Example 5

Cystic Fibrosis Screening Assay

Chinese hamster ovary (CHO) cells stably expressing both wt and ΔF508 CFTR were used in these assays. The cultures were grown on 100 mm plastic cell dishes in DMEM containing 10% foetal bovine serum (FBS) and kept at 5% $CO_2$/95% $O_2$ at 37° C. Cells were grown to confluence and used 3-5 days post-plating. All test compounds were added to cells for 24 hours prior to analysis.

For most studies, compounds of formula (I) were applied to the cells for 72 hours, with fresh media and drug applied every 24 hours. Compounds of formula (I) were dissolved in DMSO at a stock concentration of 20 mM.

CHO cells stably transfected with ΔF508 CFTR showed little band B and no band C CFTR. As a control, sodium butyrate (5 mM) increased band B, with no discernable increase in band C. 7-Phenyl-2,4,6-heptatrienoylhydroxamic acid at a concentration of 60 μM gave a slight increase in band B with no change in band C. At a concentration of 100 μM, the amount of band B increased with no change in band C. Similarly, 5-phenyl-2,4-pentadienoylhydroxamic acid at 60 μM increased band B but not band C; 100 μM of 5-phenyl-2,4-pentadienoylhydroxamic acid gave a proportionate increase in band B.

Immunoblot analysis of CFTR reveals changes in total cellular CFTR content, but does not reflect whether such changes in CFTR are reflected by changes in cell surface expression. To assess cell surface expression, a cell surface biotinylation protocol was employed. A faint band for band B CFTR was detectable at the cell surface for wild-type CFTR. Exposure of CHO cells to reduced temperature or butyrate had marginal effects on cell surface CFTR, despite apparent changes in total cellular CFTR. In contrast, both 5-phenyl-2,4-pentadienoylhydroxamic acid and 7-phenyl-2,4,6-heptatrienoylhydroxamic acid showed a dose-dependent increase in the amount of CFTR expressed at the cell surface. Only an increase in band B CFTR was observed. 7-Phenyl-2,4,6-heptatrienoylhydroxamic acid appeared to have a greater effect on total CFTR levels. 5-Phenyl-2,4-pentadienoylhydroxamic acid appeared to have a greater effect on cell surface CFTR expression. Both 5-phenyl-2,4-pentadienoylhydroxamic acid and 7-phenyl-2,4,6-heptatrienoylhydroxamic acid increase cellular CFTR and expression of CFTR at the cell surface.

Example 6

Bronchial Epithelial Cell Electrolyte Transport

Studies were carried out using human bronchial epithelial (HBE) cells derived from five cystic fibrosis (CF) patients and five nonCF patients. The protocol is described in Devor, D. C. et al., "Pharmacological modulation of ion transport across wild-type and DeltaF508 CFTR-expressing human bronchial epithelia," Am. J. Physiol. 279: C461-C479, 2000.

Cells were isolated and grown on filters for short circuit current (Isc) studies. Cells were mounted in modified Ussing chambers and the Isc monitored. The change in Isc in response to amiloride (10 μM) was taken as a measure of net electrogenic sodium transport after equilibration for 20 minutes. Forskolin (2 μM), UTP (100 μM), and genistein (30 μM) were used to stimulate anion secretion. Results from 6 to 12 similar experiments were obtained.

7-Phenyl-2,4,6-heptatrienoylhydroxamic acid (30 mM) was added to the culture medium and the cells were incubated for 24, 48, and 72 hours. Cells were fed every 24 hours with fresh media containing the compound. Control cells received an equivalent amount of vehicle (DMSO). Short circuit current measurements were also made on T84 cells, a human colonic epithethial cell line that secretes chloride by a CFTR mediated mechanism, and on M1 cells, a mouse kidney cell line that absorbs sodium by an ENaC mediated mechanism.

Table 2 summarizes the results from CF HBE cells treated for 72 hours with 30 μM 7-phenyl-2,4,6-heptatrienoylhydroxamic acid relative to the control (untreated) cells. Electrogenic sodium transport was estimated from the amiloride (5 μM) sensitive short circuit current. The CFTR genotype for patient 1 was heterozygous ΔF508-CFTR/2183deleteAA>GCFTR, and the CFTR genotype for patients 2-5 was homozygous ΔF508-CFTR/ΔF508-CFTR. In every case, 7-phenyl-2,4,6-heptatrienoylhydroxamic acid caused a substantial inhibition in sodium transport. For example, 7-phenyl-2,4,6-heptatrienoylhydroxamic acid caused a 53% inhibition in sodium transport in the cells derived from ΔF508/2183deleteAA>GCFTR heterozygous patient 1, and a 100% inhibition in cells derived from ΔF508-CFTR homozygous patient 2.

TABLE 2

| Patient # | % Inhibition of Sodium Transport |
| --- | --- |
| 1 | 53% |
| 2 | 100% |
| 3 | 53% |
| 4 | 58% |
| 5 | 82% |
| Mean ± SEM | 69.2 ± 29.99% |

Inhibition of sodium transport by 7-phenyl-2,4,6-heptatrienoylhydroxamic acid was concentration-dependent with a half-maximal inhibitory concentration of 11.9 μM±3.31 μM (n=3 patients with 6 filters from each treated for 72 hours). The inhibition of sodium transport was also time dependent with a half-maximal inhibition at 24 hours of treatment and complete inhibition at 48 and 72 hours. When directly added to the Ussing chamber, 7-phenyl-2,4,6-heptatrienoylhydroxamic acid had no effect on sodium transport over a 90 minute inhibitory period ($T_0$Isc 46±3.6 μA/cm² versus $T_{90}$ 67±1.5 μA/cm², n=3). 7Phenyl-2,4,6-heptatrienoylhydroxamic acid did not alter the transepithelial resistance (control 537±17.8 Ωcm² versus treated 544±23.1 Ωcm², n=18).

Control experiments were performed with T84 cells and M1 cells. T84 cells secrete chloride in response to cAMP via a CFTR mediated mechanism. 7-Phenyl-2,4,6-heptatrienoylhydroxamic acid had no effect on chloride secretion by T84 cells after a 72 hour treatment (control 102±10 μA/cm² versus treated 102±11 μA/cm², n=3) nor after a 90 min exposure in the Ussing chamber. M1 cells absorb sodium by an ENaC mediated mechanism. 7-Phenyl-2,4,6-heptatrienoylhydroxamic acid had no effect on sodium transport in M1 cells.

The effects of three reference compounds were also evaluated. Trichostatin, a potent histone deacetylase inhibitor (low nM $K_i$) had no effect on sodium transport at 3 nM, 30 nM, and 100 nM, but caused a significant degree of inhibition (84%) at 1 μM in HBE cells treated for 72 hours. 7-Phenyl-2,4,6-heptatrienoic acid at concentrations up to 100 μM and treatment periods of 72 hours had no effect on sodium transport or anion secretion in CF HBE cells. 4-phenyl butyrate (1 to 3 mM) caused a 3-fold increase in sodium transport for 24 to 72 hours. 4-phenyl butyrate failed to increase anion secretion in CF HBE cells.

Table 3 summarizes the results of treating non-CF cells derived from COPD patients with 30 μM 7-phenyl-2,4,6-heptatrienoylhydroxamic acid for 72 hours. Electrogenic sodium transport was estimated from the amiloride (5 μM) sensitive short circuit current. Anion secretion was estimated from the forskolin (2 μM) stimulated short circuit current after the addition of amiloride. The treatment of cells with 30 μM 7-phenyl-2,4,6-heptatrienoylhydroxamic acid for 72 hours caused an inhibition in the amiloride sensitive sodium transport of nearly 80%. This effect was concentration and dose dependent with a half-maximal inhibition concentration of 13 μM±3 μM and a half-maximal inhibition at 24 hours.

TABLE 3

| Patient # | % Inhibition of Sodium Transport | % Control Anion Secretion |
| --- | --- | --- |
| 1 | 51% | 112% |
| 2 | 87% | 85% |
| 3 | 87% | 144% |
| 4 | 99% | 104% |
| 5 | 73% | 71% |
| Mean ± SEM | 79.4 ± 8.32% | 103 ± 12.5% |

Trichostatin (1 μM) inhibited sodium transport by 70%. 7-Phenyl-2,4,6-heptatrienoic acid had no effect on sodium transport or anion secretion in the non-CF HBE cells. 4-phenyl butyrate caused a 3-fold increase in sodium transport and a 2-fold increase in anion secretion.

The above results indicate that compounds including an oxyamide linkage in an amount effective to inhibit sodium ion transport can be used to decrease sodium transport in pulmonary epithelial cells and treat airway diseases including cystic fibrosis (CF), chronic obstructive pulmonary disease (COPD), asthma, and acute and chronic bronchitis. Unexpectedly, 7-phenyl-2,4,6-heptatrienoylhydroxamic acid can be used to inhibit sodium transport in the airways in vivo without having undesired effects on renal sodium transport. 7-Phenyl-2,4,6-heptatrienoylhydroxamic acid can be delivered systemically or by inhalation for the treatment of airway diseases, for example, at a plasma concentration of at least 10 μM sustained for a period of at least 24 hours, and can be administered, for example, with a dose at every six hours. Trichostatin (e.g., at 1 μM), SAHA, or other oxyamide containing compounds can also be used to decrease sodium transport in pulmonary epithelial cells and treat airway diseases.

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of inhibiting sodium ion transport in an airway epithelial cell comprising contacting the cell with a compound including a zinc-binding moiety in an amount effective to inhibit sodium ion transport and to inhibit a histone deacetylase in a cell, wherein the compound includes an oxyamide linkage and a $C_{4-10}$ hydrocarbon chain containing at least two carbon-carbon double bonds and wherein the compound is of formula (I)

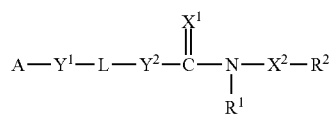

wherein
A is a cyclic moiety selected from the group consisting of aryl, or heteroaryl
$Y^1$ is —$CH_2$—, —O—, —$N(R^a)$—, or a bond, and $Y^2$ is —$CH_2$—, —O—, or —$N(R^c)$—; each of $R^a$ and $R^c$, independently, being hydrogen, alkyl, alkenyl, alkynyl, alkoxy, hydroxylalkyl, hydroxyl, or haloalkyl;
L is the $C_{4-10}$ hydrocarbon chain containing at least two carbon-carbon double bonds:
$R^1$ is hydrogen;
$R^2$ is hydrogen; and
each of $X^1$ and $X^2$, independently, is —O—;
or a pharmaceutically acceptable salt thereof,
in an amount effective to inhibit sodium ion transport.

2. A method of treating lung disease in a mammal comprising administering to the mammal an effective amount of a compound including a zinc-binding moiety to treat lung disease and to inhibit a histone deacetylase in a cell, wherein the compound includes an oxyamide linkage and a $C_{4-10}$ hydrocarbon chain containing at least two carbon-carbon double bonds and wherein the compound is of formula (I)

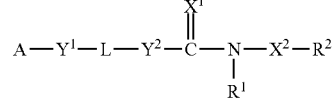

wherein
A is a cyclic moiety selected from the group consisting of aryl, or heteroaryl
$Y^1$ is —$CH_2$—, —O—, —$N(R^a)$—, or a bond, and $Y^2$ is —$CH_2$—, —O—, or —$N(R^c)$—; each of $R^a$ and $R^c$, independently, being hydrogen, alkyl, alkenyl, alkynyl, alkoxy, hydroxylalkyl, hydroxyl, or haloalkyl;
L is the $C_{4-10}$ hydrocarbon chain containing at least two carbon-carbon double bonds:
$R^1$ is hydrogen;
$R^2$ is hydrogen; and
each of $X^1$ and $X^2$, independently, is —O—;
or a pharmaceutically acceptable salt thereof.

3. The method of claim 1, wherein A is phenyl, furyl, thienyl, pyrrolyl, or pyridyl.

4. The method of claim 2, wherein A is phenyl, furyl, thienyl, pyrrolyl, or pyridyl.

* * * * *